(12) United States Patent
Ben-Amotz et al.

(10) Patent No.: US 6,483,581 B1
(45) Date of Patent: Nov. 19, 2002

(54) RAMAN SYSTEM FOR RAPID SAMPLE INDENTIFICATION

(75) Inventors: Dor Ben-Amotz, W. Lafayette, IN (US); Yanan Jiang, West Lafayette, IN (US); Edward R. Grant, West Lafayette, IN (US); Ken Haber, West Lafayette, IN (US); George M. Laurence, Jr., West Lafayette, IN (US)

(73) Assignee: Spectra Code, Inc., West Lafayette, IN (US)

( * ) Notice: Subject to any disclaimer, the term of this patent is extended or adjusted under 35 U.S.C. 154(b) by 0 days.

(21) Appl. No.: 09/446,673

(22) PCT Filed: Jul. 2, 1998

(86) PCT No.: PCT/US98/13856

§ 371 (c)(1),
(2), (4) Date: Dec. 22, 1999

(87) PCT Pub. No.: WO99/01750

PCT Pub. Date: Jan. 14, 1999

Related U.S. Application Data

(60) Provisional application No. 60/051,533, filed on Jul. 2, 1997.

(51) Int. Cl.$^7$ .................................................. G01J 3/44
(52) U.S. Cl. ........................................ 356/301; 356/328
(58) Field of Search .................................. 356/301, 328

(56) References Cited

U.S. PATENT DOCUMENTS

| | | | |
|---|---|---|---|
| 3,951,526 A | * | 4/1976 | Grossman .................... 359/851 |
| 4,573,761 A | | 3/1986 | McLachlan et al. |
| 4,802,761 A | | 2/1989 | Bowen et al. |
| 4,974,209 A | | 11/1990 | Hoult |
| 5,096,634 A | | 3/1992 | Tsadares et al. |
| 5,112,127 A | | 5/1992 | Carrabba et al. |
| 5,256,880 A | | 10/1993 | Loree et al. |
| 5,262,644 A | | 11/1993 | Maguire |
| 5,404,218 A | | 4/1995 | Nave et al. |
| 5,419,438 A | | 5/1995 | Squyres et al. |

(List continued on next page.)

FOREIGN PATENT DOCUMENTS

| | | |
|---|---|---|
| DE | 43 00 169 | 7/1994 |
| EP | 0 758 084 A2 | 2/1997 |
| WO | WO 96/06346 | 2/1996 |
| WO | WO 96/29925 | 10/1996 |

Primary Examiner—Frank G. Font
Assistant Examiner—Roy M. Punnoose
(74) Attorney, Agent, or Firm—Brinks Hofer Gilson & Lione (57) ABSTRACT

A hand-held material identification apparatus 10 uses a spectrograph and detector array detecting a Raman spectrum produced by a sample illuminated by a laser source to recognize a variety of materials with a command to recognition time cycle of about one second or less. The width of the spectrum detected by each detector in the array is less than $\frac{1}{4}^{th}$ the excitation source wavelength deviation to permit smoothing of the spectrum detected by the discrete spectral elements to eliminate pixel noise without loss of Raman spectral information. The Raman spectra are produced by materials illuminated by an inexpensive near-infrared multimode laser operated in a pulse mode to deliver between 0.05 and 0.5 joules of photon energy, with the Raman spectra being detected before any significant heating of the sample occurs. The identification apparatus 10 qualitatively determines the chemical composition of reinforced and unreinforced copolymers and composites such as ABS, polypropylene, talc-filled polypropylene, polycarbonate, PMMA, polyethylene, and PVC, from samples of different colors and textures with a high degree of success without the need for special positioning or sample preparation.

30 Claims, 9 Drawing Sheets

U.S. PATENT DOCUMENTS

| | | |
|---|---|---|
| 5,443,164 A | 8/1995 | Walsh et al. |
| 5,459,313 A | 10/1995 | Schrader et al. |
| 5,510,619 A | 4/1996 | Zachmann et al. |
| 5,512,752 A | 4/1996 | Aikawa et al. |
| 5,534,997 A | 7/1996 | Schrader |
| 5,615,673 A | 4/1997 | Berger et al. |
| 5,641,072 A | 6/1997 | Otake |
| 5,646,411 A | 7/1997 | Kain et al. |
| 5,710,626 A | 1/1998 | O'Rourke et al. |
| 5,713,364 A | 2/1998 | DeBaryshe et al. |
| 5,804,813 A | 9/1998 | Wang et al. |
| 5,813,987 A | 9/1998 | Modell et al. |
| 5,822,061 A | 10/1998 | Delhaye et al. |
| 5,847,400 A | 12/1998 | Kain et al. |
| 5,862,287 A | 1/1999 | Stock et al. |
| 5,866,430 A | 2/1999 | Grow |
| 5,949,532 A | 9/1999 | Schrof et al. |
| 5,963,319 A | 10/1999 | Jarvis et al. |
| 6,006,001 A | 12/1999 | Alfano et al. |
| 6,028,667 A | 2/2000 | Smith et al. |
| 6,100,975 A | 8/2000 | Smith et al. |
| 6,313,423 B1 * | 11/2001 | Sommer et al. ............ 209/577 |

* cited by examiner

Fig. 9a
HDPE

Fig. 9b
Sugar

Fig. 9c
Aspirin

Fig. 10a  HDPE-vector

Fig. 10b  Sugar-vector

Fig. 10c  Aspirin-vector

FIG. 11

RAMAN SYSTEM FOR RAPID SAMPLE INDENTIFICATION

CROSS REFERENCE TO RELATED APPLICATION

This application is related to U.S. Provisional Application Ser. No. 60/051,533 filed Jul. 2, 1997.

BACKGROUND OF THE INVENTION

The present invention relates generally to applied optics, spectra-chemical image processing, chemical identification, and chemical analysis. More specifically, the present invention relates to apparatus and methods for the non-destructive testing and identification of the composition of a sample of plastics or other materials using Raman spectroscopy and computerized signal processing.

A widespread need exists in industry and government for identifying materials. For example, automobile companies and plastics manufactures must identify and separate plastic resins in recycling operations. Pharmaceutical companies must monitor chemical constituents during drug production. Monitoring agencies and firms must assay waste stream flows into the environment. Law enforcement agencies must identify the presence of illicit drugs in the field in order to combat criminal drug trafficking.

In today's environmentally conscious society, simple economics provides a strong incentive for manufacturers to minimize their use of natural resources and public landfills. Substantial economic benefit can be gained by turning to recycling as a source for raw materials and as the ultimate repository for the manufactured goods. Using recycled raw materials in products can increase profits by saving materials costs and energy. Efficiently recycling packaging and production waste can save landfill charges and provide a cost recovery stream. Further, manufacturing goods with recycled content, and designing goods that themselves are recyclable, is a civic duty that also offers public relations benefits that are worthwhile from a marketing standpoint.

Many suppliers, however, face difficulties in using recycled feed streams. All companies face competition, and in the marketplace, price alone does not guarantee market share. Most manufacturers value quality and consistency of goods more than the abstract notions of civic duty and environmental policy. Further, many production lines operate with just-in-time inventories, in which a factory receives all the components necessary to assemble a product only hours before they are needed. The presence of only a few defective parts can shut down a production line until replacement parts arrive. Such a shut down can cost a manufacturer many thousands of dollars.

Thus, it is easy to understand why companies have been reluctant to include recycled materials in products. Recycled materials must have documented histories so that they are assured of compatibility with the manufacturing process. A misidentified piece of recycled material included with virgin material can destroy an entire production run. Maintaining the history of recycled goods, or even knowing their exact composition is difficult, if not impossible, with current technology.

Millions of tons of plastic and other materials are deposited in landfills or incinerated every year due almost solely to the lack of sufficient technology to avoid cross contamination between different types of plastic or other material during collection. The need therefore exists for an effective, economical means to identify a variety of materials, and-specifically plastics, on site in scrap yards, warehouses, factories and recycling centers. The successful commercialization of an instrument with such capabilities would greatly increase the recycling rates for plastics and perhaps many other materials. By offering a simple means to overcome the difficult problem of material identification, the present invention seeks to help make manufacturers more receptive to including recycled content in their products, and purchasers more confident of the quality of those products.

Many methods exist for identifying materials. One test for plastic materials, for example, involves the burning of a small sample of the plastic material. Upon smelling the smoke, a trained technician can identify several different classes of plastics with reasonable success. While this method can be employed in a laboratory, such methods are not appropriate or practical for commercial or production line applications. This type of chemical analysis would also not be acceptable to law enforcement personnel or the courts for the identification of Cocaine.

An assortment of analytical identification methods exist, such as Fourier Transform Infrared Spectroscopy (FTIR) and X-ray fluorescence (XRF), for the non-destructive testing of materials. An example of FTIR technology is disclosed in U.S. Pat. No. 5,510,619. While well known and used, the FTIR process is not practical in many commercial applications because the method is very sensitive to dirt, surface roughness, coatings, moisture, and sample motion during identification. The XRF process is also used but it is relatively expensive. Other analytical identification methods are disclosed, for example, in U.S. Pat. No. 5,256,880 and 5,512,752.

Raman spectroscopy, discovered by C. D. Raman in 1928, has many unique qualities that can be advantageously employed in the practical identification of materials. Raman signals, generated by the interaction of monochromatic light and a sample, are not affected by dirt, surface finish, coatings, or any motion of the sample being identified. Significantly, Raman signals are also not as sensitive to water, glass or quartz as other infrared signals. As a result, chemical samples can be contained within a glass vessel, or even suspended in an aqueous solution without affecting the Raman signal. The Raman process also has a significantly higher depth of field than other processes and can "look through" a container to the chemical sample contained inside.

Despite these advantages, Raman spectroscopy is not widely used because of a low signal to noise ratio inherent in Raman Spectroscopy. Traditionally, the excitation light source, typically a laser, is directed continuously against a chemical sample, and the Raman signal is collected over time. An example of such an apparatus is disclosed in U.S. Pat. No. 5,534,997. Increasing the power of the excitation laser in the Raman process can increase the strength of the Raman signal and reduce the required sampling time. However, the increase in power can cause thermal damage to the sample particularly if the sample has low thermal conductivity that is typical of plastics. The increase in power can also cause "black body" or thermal radiation that can overwhelm the Raman signal. It is commonly assumed, therefore, that Raman spectroscopy is not appropriate for the practical identification of highly energy absorbent materials such as black or highly pigmented plastics. In the extreme case, such highly absorbent materials can char or burn thus rendering the material unsuitable for further use.

What is needed is a system for analyzing and identifying the composition of a wide variety of materials that is fast enough for practical application in a commercial setting, insensitive to sample impurities or surface imperfections, tolerant of water and common sample containers, and which does not damage the sample being analyzed and identified.

SUMMARY OF THE INVENTION

A system satisfying these needs generally comprises a probe including a housing having an optical window through which visible and infrared light can pass. A monochromatic light source is provided with radiation optics optically coupling the light source to the optical window so that light emitted from the light source is directed through the window toward a sample causing the sample to produce a characteristic Raman signal. Sampling optics are coupled to the optical window to receive the characteristic Raman signal produced from the sample including at least one filter for removing unwanted spectral portions. A spectrograph is coupled to the sampling optics for dispersing the characteristic Raman signal into a spectrum to form a spectrographic output. An optical detector is coupled to the spectrograph to receive the spectrographic output and generate a digital map representing the Raman spectrum as a function of wavelength. A computer is coupled to the detector that includes an input to receive the digital map, a library of digital maps of specimens of known composition, a comparison means for comparing a received digital map with the contents of the library to select any match exceeding a specified confidence level, and an output display of the name of the selected match. A trigger circuit is included that initiates collection of the spectrographic output by the detector at the same time or slightly before it initiates emission by the light source so that data concerning the characteristic Raman signal from the sample can be collected by the detector before any significant heating of the sample can take place. The trigger circuit initiates selectively one or more pulses of light from the light source of specified duration and power so as to avoid or reduce the black body or thermal radiation problem commonly experienced with other apparatus. The apparatus is suitable for use to identify a wide variety of materials in gas, liquid, solid, or powder form, including polymers, plastics, ceramics, minerals, composites, pharmaceuticals, petrochemicals, organics, inorganics, biochemicals, and organo-metallics.

The present invention advantageously employs one or more discrete pulses of light, preferably generated by a laser, to cause the Raman signal to be produced by a sample. The monochromatic light source preferably comprises an inexpensive near-infrared multimode laser operable in a pulse mode between a lower and an upper intensity. The lower intensity level is at or just above the threshold intensity below which laser activity discontinues, typically less than about 105% of the lasing threshold. The upper intensity can be at any level at or below a maximum intensity established by the upper power limit of the laser. A "lapse time" or "off time" between the laser pulses is provided to allow the sample to dissipate localized heat generated by the laser pulse. Advantageously, a single location on a sample can be exposed to more than one pulse during the sampling process, and allowed to cool between pulses. The laser pulses are cycled repeatedly until an adequate Raman signal is collected to allow the required analysis to identify the sample. The pulse width defining the duration of the upper intensity can be between about 0.01 and 10.0 seconds, depending upon the nature of the sample. In the preferred embodiment employing a 1.2 Watt laser, the pulse duration is between about 80 and 120 milliseconds for materials sensitive to optical damage. For less sensitive materials, a typical pulse duration can be up to about 500 milliseconds. The pulse duration can be shortened by using a correspondingly higher power laser to deliver between about 0.05 to 0.5 joules of photon energy to the sample. The number and duration of pulses employed to test a given sample is controlled to provide a satisfactory Raman signal while minimizing the thermal strain on the sample and avoiding detector saturation at any given pixel position. Shorter pulses and multiple discrete pulses are an important feature of the present invention which advantageously provides an enhanced Raman signal to noise ratio, even when considering sources of the same power, as the thermal noise and likelihood of detector saturation is kept to a minimum.

In a preferred embodiment of the invention, the probe housing includes a handle to permit manipulation of the probe, and further comprises a trigger situated on the handle and coupled to the light source so that depression of the trigger temporarily increases the output of light from the source, preferably in the form of one or more prescribed pulses as previously described. The apparatus preferably includes a console for housing the spectrograph, the optical detector, and the computer, and the sampling optics include a fiber-optic umbilical coupled between the console and the probe. The light source is housed in the console and the radiation optics includes at least one optical fiber carried by the fiber-optic umbilical. The probe housing preferably comprises an elongated rail having a lower and an upper surface, a longitudinal axis of the probe being separated by a fixed distance from the upper surface. A plurality of supports are fixed to the rail upper surface for supporting optical elements to intersect the longitudinal axis of the probe. The probe housing also includes a tubular member including a longitudinal slot that receives the rail so that an axis of revolution of the tubular member is coincident with the longitudinal axis of the probe and parallel to the rail upper surface. A back plate closes one end of the tubular member while a nose cone containing the optical window closes the other end. An off-axis baffling tube is supported by the rail parallel to the longitudinal axis to define a specific segregated region within the probe to permit extinction of unwanted portions of the light source spectrum immediately prior to illumination of the sample. This design allows for an ease of construction that contributes to lowering the cost of the overall system sufficiently to permit widespread adoption of the system by both industry and government.

In the preferred embodiment, the optical elements held by the plurality of supports within the probe can include lenses providing the probe with a prescribed depth of field, at least one filter, and a reflective element inclined with respect to the longitudinal axis of the probe for aligning the laser output with the optical window. To achieve optimum Raman signals, the lenses uniformly distribute the laser output over a sample irradiation area so as to achieve a power density of between about 1 $mW/mm^2$ and 1 $W/mm^2$. This is achieved by employing lenses having an f-number of between about 1 and 3. Preferably, the sampling optics includes a plurality of optical fibers, each of the fibers including an entrance end and an exit end. The entrance ends of the optical fibers are situated in a compact array in a common plane within the probe housing so as maximally to collect the Raman signal produced by the sample. The exit ends of the optical fibers are arranged in a line at an entrance to the spectrograph that typically contains a diffraction grating, the ruled surface of which is aligned to be parallel with the line defined by the exit ends of the optical fibers. This feature has the advantage of providing a signal to the spectrograph that is of enhanced intensity over that which might be gathered by a single fiber yet without diminishing the spectrographic resolution. The optical detector comprises an array detector having a number of outputs sufficient to define a division of the spectrographic output into a set of discrete spectral elements having a pixel width of about 0.2 nm.

A laser particularly suitable for use with the present invention is a near-infrared (NIR) multi-mode diode laser, the wavelength and deviation of which are compatible with spectrographic identification apparatus. The use of such a laser in the present invention provides an excitation source of lower cost yet higher power and reliability than comparable single-mode diode laser. In the preferred embodiment, the laser is a 1.2 Watt, 798 nm pulsed multi-mode laser excitation source having a wavelength deviation of less than 7 nm and more typically about 1–3 nm. The use of an excitation source having a wavelength deviation significantly greater than the pixel width in the spectrographic output achieves the surprising result of simplifying the smoothing the spectrum detected by the discrete spectral elements without loss of spectral information. This smoothing function is particularly important when derivatives of the spectrum are used for comparison as the difference in wavelength permits a significant reduction in pixel noise. The ratio of excitation source wavelength deviation to spectral detection element width is desirably between about 4 and 40, and preferably between about 5 and 20. That is, the width of the spectrum detected by each pixel of the detector is less than $\frac{1}{4}^{th}$ and preferably less than $\frac{1}{5}^{th}$ the excitation source wavelength deviation.

In a typical embodiment of the present invention, the computer can be a general-purpose personal computer programmed to contain a library of digital maps of various materials of known composition. In the preferred embodiment, the digital maps consist of a second-derivative vector of the spectrographic output as a function of Raman shift wavelength smoothed to exclude the short wavelength pixel noise. The resulting second derivative is treated as an n-dimensional vector where n is the number of pixels in the spectrographic output. The computer is programmed to compare the information taken from a sample of unknown composition with the library by computing a vector dot product of the vector of the sample with each specimen vector stored in the library. The dot product constitutes a scalar evaluation of coincidence between each pair of vectors. Based on this computation, the computer can be programmed to select the best fit by merely retaining the identity of the known material having the highest value for the dot product, and displaying that identity. Where the library contains vectors of a number of very closely related materials, the computer can be programmed to retain all library-stored vectors for which the vector dot product was greater than a specified value. The computer can then conduct a review of additional criteria of the sample vector that could discriminate the retained library vectors to select the best fit. This feature, when employed by even conventional personal computers having operating speeds in the order of 300 MHz, provides an accurate identification of a wide variety of materials, typically in only 1 or 2 seconds. Where very rapid sample identification in desired, for example in automated systems, dedicated digital signal processing equipment can be employed rather than general purpose personal computers.

By offering a simple means to overcome the difficult problem of identification of materials for recycling, the present invention seeks to help make manufacturers more receptive to the idea of including recycled content in their products and give purchasers more confidence in the quality of those products. The same system programmed with a slightly different library of reference materials can enable companies to monitor a wide variety chemical constituents during manufacture and permit the assay waste stream flows into the environment for any unwanted contamination. Law enforcement agencies are also able to use the system to identify the presence of illicit drugs in the field without affecting the chemical make-up of the sample or detracting from the amount of material tested.

Additional features and advantages of the invention will become apparent to those skilled in the art upon consideration of the following detailed description of the preferred embodiment exemplifying the best mode of carrying out the invention as presently perceived.

DETAILED DESCRIPTION OF A PREFERRED EMBODIMENT

Figures 1, 2, 3:
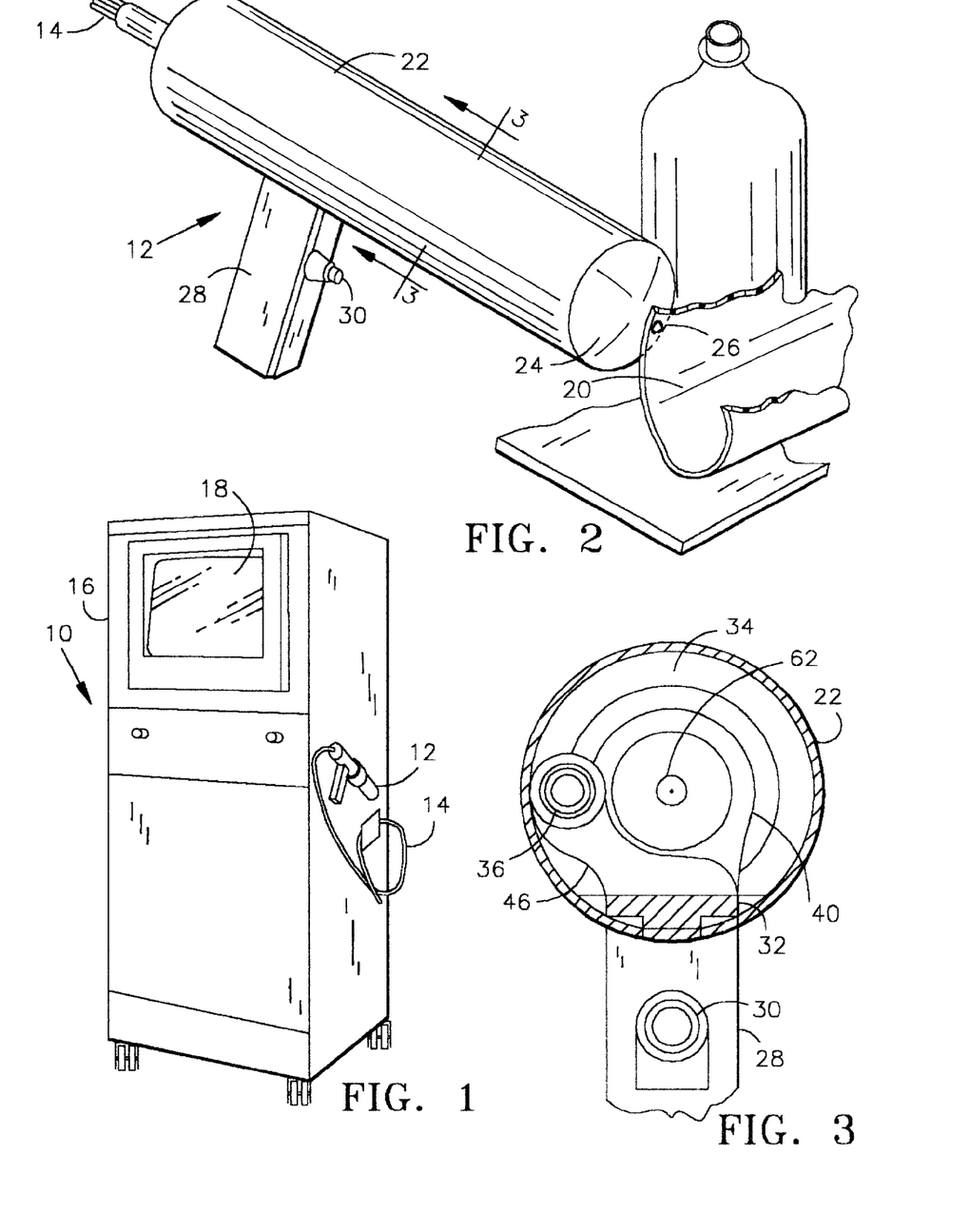
FIG. 1 is a perspective view of apparatus of the present invention showing an identification probe, a fiber-optic umbilical, and mobile console containing a laser, a spectrograph, a charge-coupled detector, and a data processing computer.
FIG. 2 is a perspective view of an identification probe of the present invention situated to test a sample.
FIG. 3 is a sectional view taken along line 3—3 of FIG. 2.

An identification apparatus 10 of the present invention includes a hand-held identification probe 12 attached by a fiber-optic umbilical 14 to an instrument console 16 that houses a laser, a spectrometer, a charge-coupled array detector, and a computer having a display screen 18. In addition, instrument console 16 is fitted with an external holder 17 to house probe 12 as shown in FIG. 1. The instrument console 16 preferably includes supporting wheels 15 so that identification apparatus 10 can easily be moved from one location to the next. It is understood, however, that the instrument console 16 may be stationary without exceeding the scope of the present invention. The instrument console 16 preferably conforms to National Electrical Manufacturers Association-12 specifications so that console 16 protects the instruments contain therein from adverse environmental conditions. In addition, console 16 is preferably air conditioned to permit operation in extreme industrial environments.

Probe 12 is configured to illuminate and collect light scattered from solid samples 20 as shown in FIG. 2. Probe 12 includes housing 21 in the form of a generally cylindrical member 22 and includes a nose cone 24 containing an optical window 26. The optical window 26 can comprise a simple opening through which light can pass. In one preferred embodiment the optical window 26 comprises a sapphire window mounted within the aperture to protect the optics within probe 12 from airborne dust and assorted particles. The probe 12 can be easily positioned relative to sample 20 by means of handle 28. A trigger 30 is situated on the handle 28 for easy operation by an operator's index finger. A longitudinal rail 32, shown in cross-section in FIG. 3, is fixed to handle 28 and provides a foundation for the optical components within the probe 12. The generally cylindrical housing member 22 includes a longitudinal slot, the edges of which contact opposing edges of the longitudinal rail 32. The housing 21 is completed by back wall 34. In the preferred embodiment, the generally cylindrical housing member 22 has an internal diameter of about 5.7 cm. It is understood, however, that the internal diameter of housing member 22 can vary in accordance with the constraints imposed on the system by its intended use as well as the components to be housed therein. In the preferred embodiment, the housing member 22, nose cone 24, longitudinal rail 32, and back wall 34 are construction of aluminum that has been black anodized. A variety of metals, copolymers, and composites may be used, however, to construct probe 12 in accordance with the present invention.

Figure 4:
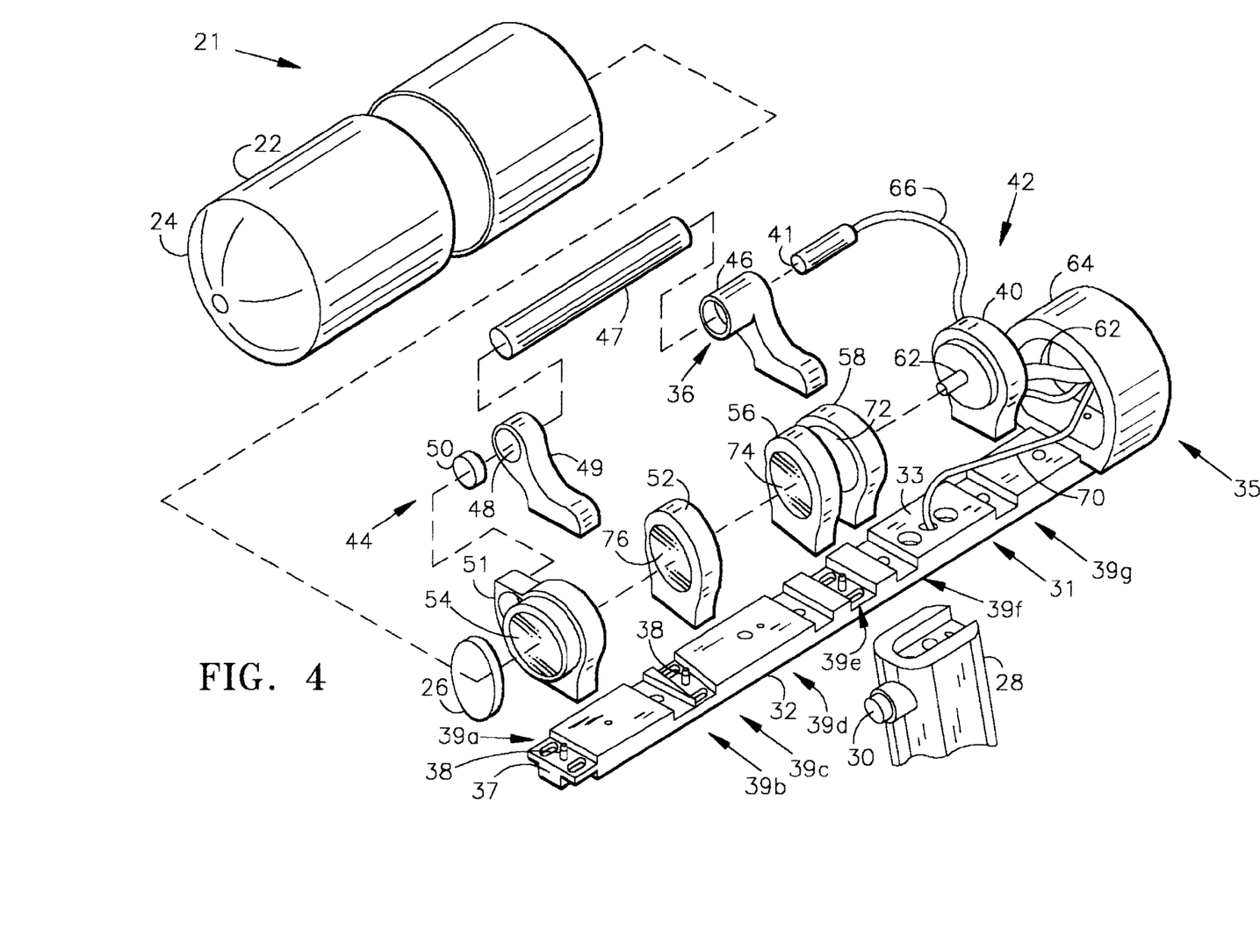
FIG. 4 is an exploded perspective view of an identification probe of the present invention.
Figure 5:
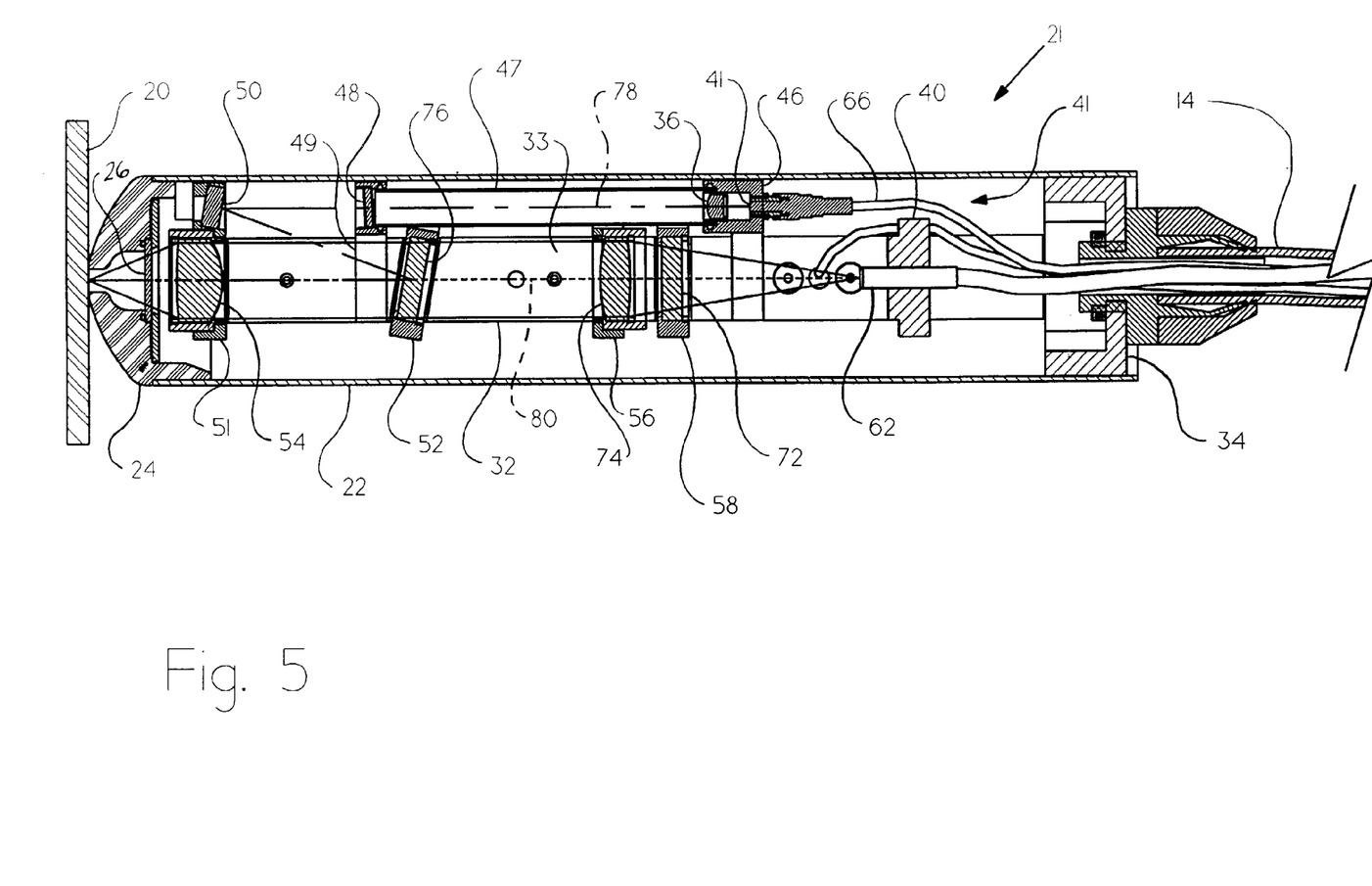
FIG. 5 is a horizontal sectional view of the identification probe shown in FIG. 4.
Figure 6:
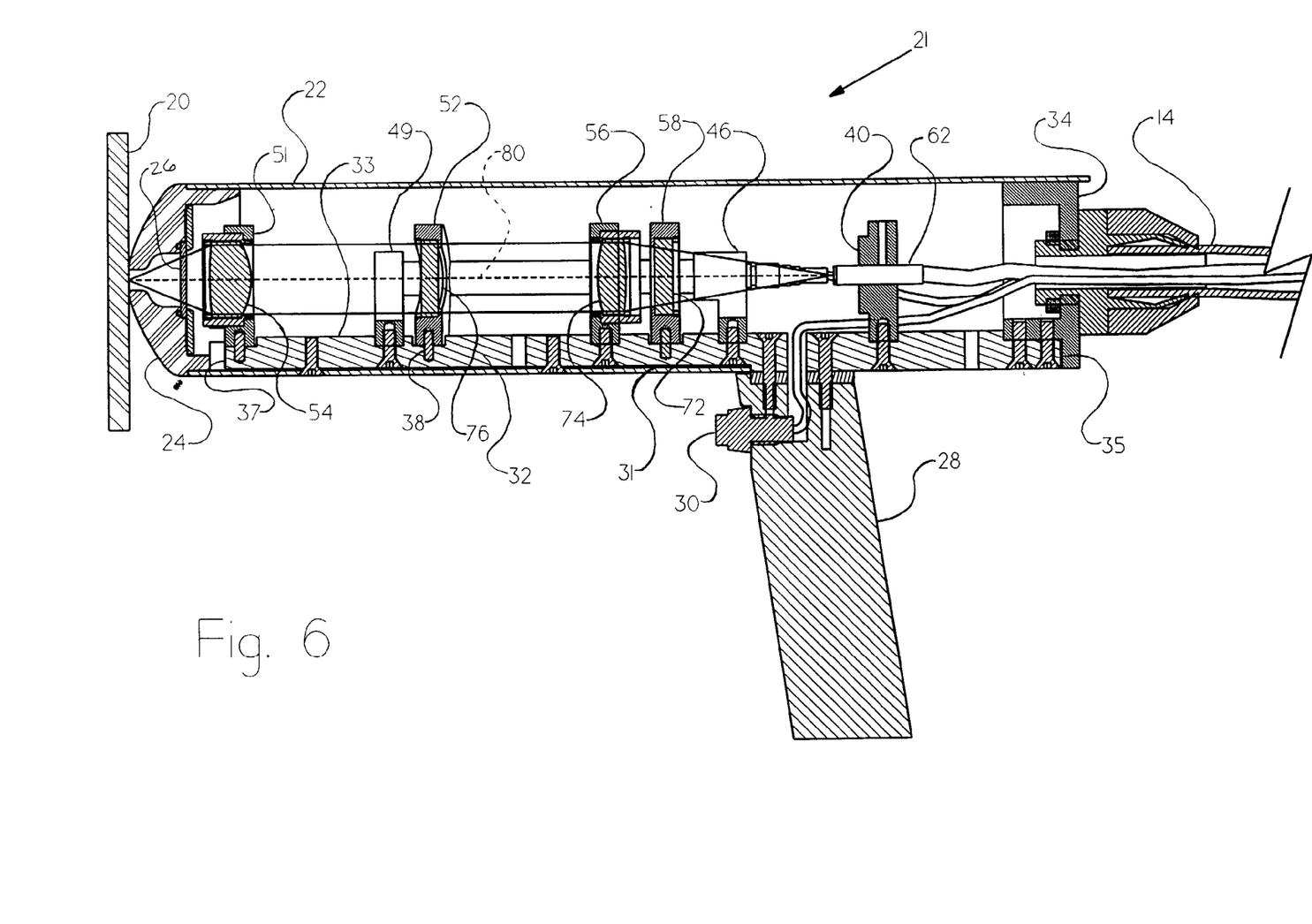
FIG. 6 is a vertical sectional view of the identification probe shown in FIG. 4.

The longitudinal rail 32 includes a lower surface 31, an upper surface 33, a rearward end 35, and a forward end 37 as shown in FIGS. 4–6. A plurality of lateral slots 39a through 39g are milled into the upper surface 33 of the longitudinal rail 32 generally perpendicular to the length dimension of the longitudinal rail 32, except slot 39c which is inclined at an angle of about 10°. Pivot pins 38 are fixed in the center of each of the lateral slots 39a, 39c, and 39e to permit small adjustments in the alignment of the supports fastened therein. Support 40 is fastened in slot 39g to hold the entrance end of optical fiber bundle 62 that carries the characteristic Raman signal produced from a sample through the fiber-optic umbilical 14 to the instruments within console 16. Support 46 is fastened in slot 39f to hold lens 36 adjacent the exit end 41 of optical fiber 66 carrying light from the laser source housed in the console 16. Support 58 is fastened in slot 39e to hold an optical filter 72, such as a holographic notch filter or long pass filter, that selectively rejects light at the wavelength of the laser source but transmits light of longer wavelength. Support 56 is fastened in slot 39d to hold a lens 74 having a focal length selected to direct the Raman signal on the entrance end of optical fiber bundle 62. Support 52 is fastened in slot 39c to hold optical filter 76, such as an interference or holographic filter and preferably a long pass filter designed to transmit light having a wavelength longer than the laser source and reflect all light having a wavelength equal to or less than the wavelength of the laser source. Support 49 is fastened in slot 39b to hold a band pass filter 48 which controls the wavelength deviation of the source light directed toward the sample 20. Support 51 is fastened in slot 39a to hold lens 54 and mirror 50.

Supports 46 and 49 also support the ends of baffling tube 47 creating a specific segregated region within the housing 21 between the lens 36 and band pass filter 48. Essentially monochromatic light from a laser source follows a first optical path 78 defined in part by the radiation optics 44 within probe 12, shown in FIG. 5. Any light from the source transmitted by fiber end 41 that is rejected by band pass filter 48 is absorbed by the interior of the baffling tube 47. This is accomplished by constructing the baffling tube 47 to have a light absorbent interior surface, and inclining the band pass filter 48 with respect to the axis 78 by a small angle, typically about 3°. The small inclination of band pass filter 48 also ensures that any light reflected back from the sample past mirror 50 is extinguished on the interior of the baffling tube 47, and is not directed toward end 41 of optical fiber 66, hereby reducing or avoiding mode hopping of the source light. In the preferred embodiment, the baffling tube consists essentially of an aluminum tube that has been anodized satin black to maximize light absorbency.

Light of the correct source wavelength starts at the exit end 41 of optical fiber 66 in support 46, passes through band pass filter 48 in support 49, and reflects off of mirror 50 in support 51 toward long pass filter 76 in support 52. The reflective character of the long pass filter 76 for light of the wavelength of the source laser insures that the source light will be directed through lens 54 and optical window 26 to sample 20. The inclination of mirror 50 in support 51 is fixed while the inclination of supports 51 and 52 can be adjusted about pivot pins 38 to insure the desired alignment of the optical path 78. The monochromatic light is scattered by the sample 20 creating a Raman signal that is typically about 1 part in $10^6$ of the reflected and scattered incident light.

The portion of the Raman signal which is collected through optical window 26 is directed along optical axis 80 back toward fiber bundle 62 as shown in FIGS. 5 and 6. Probe 12 employs sampling optics 42 to collect the scattered Raman radiation, discriminating with an extinction ratio of about $10^6$ (1 ppm) or better for the Raman-shifted component. Imaging of the scattered light from the sample into fiber bundle 62 carried by umbilical 14 provides an depth of field of about 1 cm, which eliminates the need for precise alignment between the sample 20 and the probe 12. The front collimating lens 54 mounted in support 51 directs the Raman signal through the remaining components of the sampling optics 42 mounted on the longitudinal rail 32 to intersect the optical axis 80. The long pass filter 76 rejects substantially the entire reflected source laser light as well as all of the shorter wavelength light incoming from ambient light sources. Lens 74 focuses the signal passing through filter 76 toward the entrance end 61 of optical fiber bundle 62. Optical filter 72 further extinguishes the reflected incident light from the laser source so that a substantial portion of the signal entering the entrance end of optical fiber bundle 62 is the Raman signal produced by the sample 20.

Figure 11:
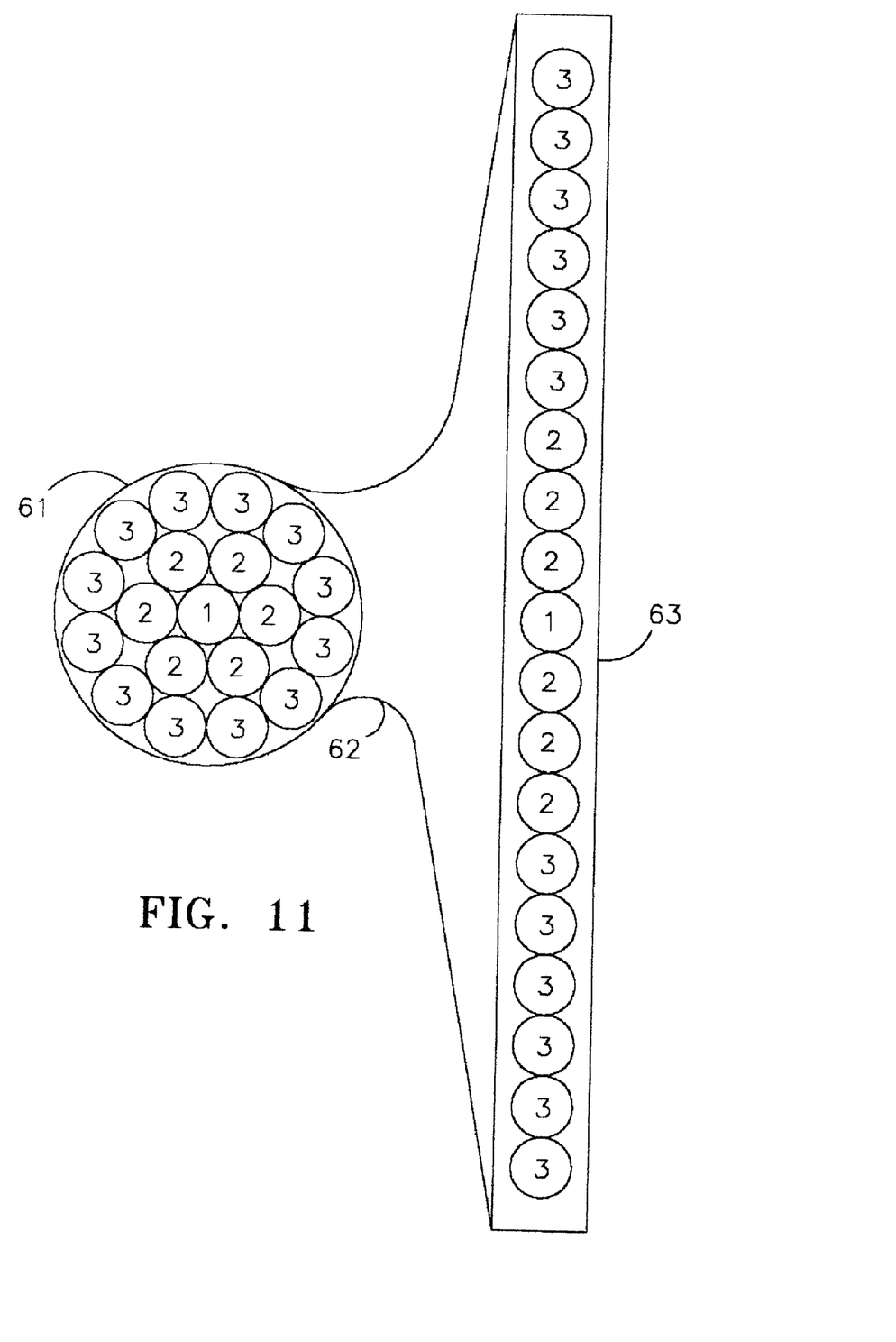
FIG. 11 is a schematic view of the fiber bundle employed in the sampling optics showing the preferred mapping of the optical fibers at the two ends of the fiber bundle.

The probe 12 is coupled to instrument console 16 by fiber-optic umbilical 14. Umbilical 14 includes the mapped optical fiber 62 that delivers the scattered Raman radiation from probe 12 to a spectrograph located in the console 16. Fiber bundle 62 preferably includes nineteen fibers arranged in a close-packed configuration of one fiber surrounded by six fibers surrounded by twelve fibers as shown in detail in FIG. 11. Each of the fibers includes an entrance end 61 positioned to lie within probe 12 in a common plane, an exit end 63 positioned to lie within console 16, and a middle portion extending there between. The umbilical 14 enters probe 12 through an opening formed in back plate 34 of housing 21. The umbilical 14 also includes the optical fiber 66 that carries the light emitted by the source laser located in the console 16. The umbilical 14 also carries a communication link between trigger 30 and the console 16, which generally takes the form of a two wire cable 70 that connects trigger 30 is series with an electrical control circuit in console 16.

Figure 7:
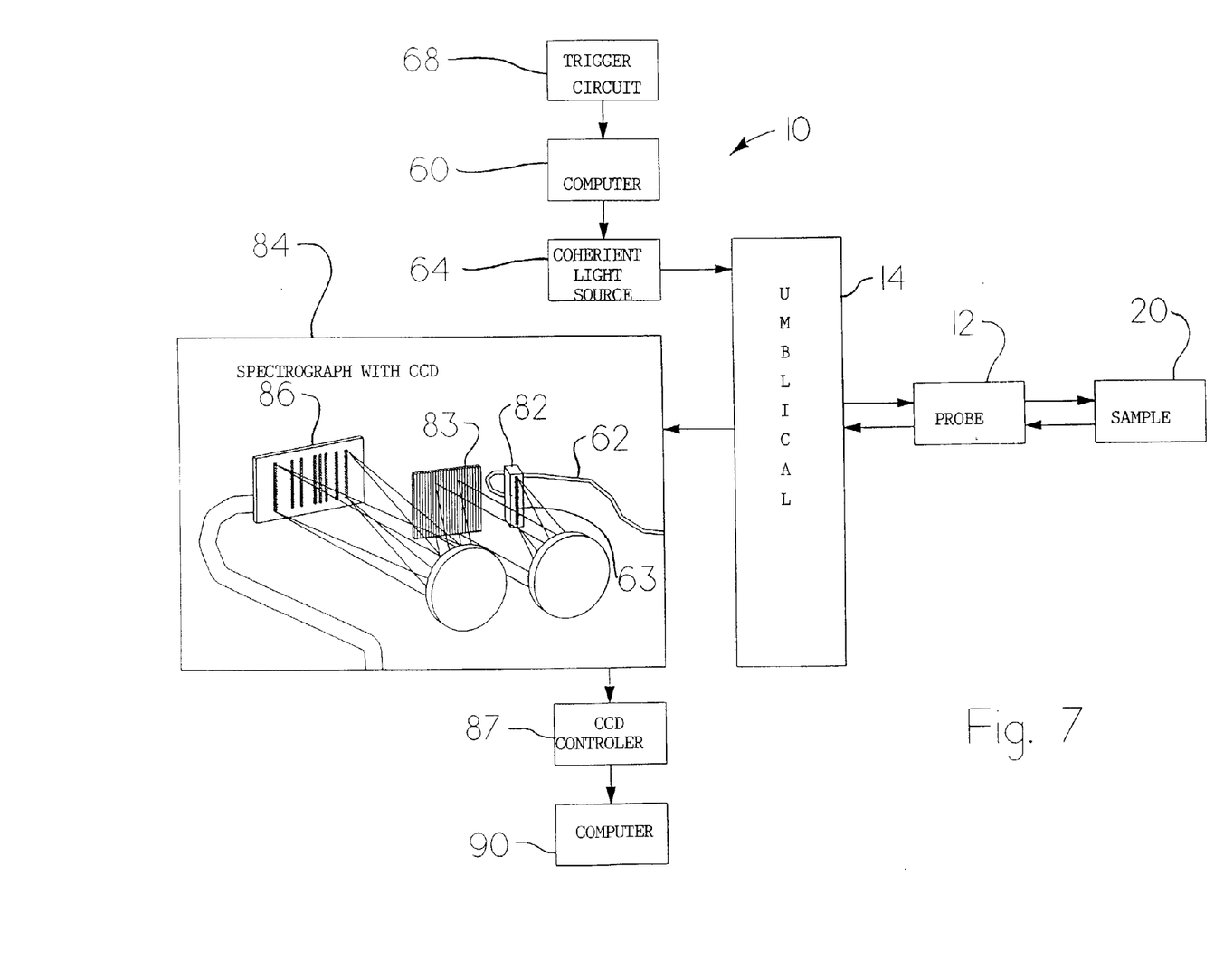
FIG. 7 is a diagrammatic view of the principal elements included in an apparatus of the present invention.

A coherent light source 64 suitable for use with the present invention is a near-infrared (NIR) Raman excitation laser illustrated schematically in FIG. 7. NIR lasers are preferred as they minimize the absorption and fluorescence of plastics, pigments, and surface impurities. The use of a multi-mode diode laser, the deviation of which is compatible with spectra-chemical identification of plastics and composites, provides the user with lower cost and higher reliability than a single-mode diode laser. In the preferred embodiment, laser 64 is a 1.2 Watt, 798 nm pulsed multi-mode laser excitation source. Laser 64 produces an identifiable signal from almost all materials with a fraction of a second exposure. It is understood, however, that laser 64 may also be of higher power so long as the pulses are shortened so that between about 0.05 and 0.5 joules of photon energy are delivered to the sample. The laser 64 is actuated by a triggering circuit 68 coupled to trigger 30 and in conjunction with computer 60.

The triggering circuit 68 initiates the operation of the laser 18 which operates in a pulse mode between a lower and an upper intensity. The lower intensity is a rest mode just at or slightly above the threshold below which laser activity is discontinues in the laser. The upper intensity can be adjusted to any level at or below a maximum intensity established by the upper power limit of the laser. The triggering circuit 68 in conjunction with the computer 60 can define the shape and duration of the pulse as well as a minimum "lapse time" or "off time" between the laser pulses to allow the sample 20 to dissipate localized heat generated by the laser pulse. Advantageously, a single location on a sample 20 can be exposed to more than one pulse during the sampling process, and allowed to cool between pulses. The laser pulses are cycled repeatedly either in response to a continuous depression of the trigger 30, or as quickly as the trigger 30 is depressed, but not more often than permitted by the lapse time setting, until an adequate Raman signal is collected to allow the required analysis to identify the sample. The pulse width defining the duration of the upper intensity can be between about 0.01 and 10.0 seconds, and preferably between about 75 and 750 milliseconds. Typically, the number of pulses employed to test a given sample can be in the range of from 1 to about 30. By controlling the pulse duration and lapse time, the triggering circuit defines a range of power densities that can be provided at the sample surface which maximizes the Raman signal yet minimizes the thermal strain on the sample. Thus, the system 10 generally acquires a high-quality Raman spectrum of a sample or scrap of most materials with a typical exposure time of less than 500 milliseconds, typically between 80 and 120 milliseconds in the single pulse mode.

A system 10 in accordance with the present invention collects scattered laser light from a sample containing a characteristic Raman signal over a relatively large focal plane by use of a round-entrance-aperture multi-element fiber bundle 62. Collection of the Raman signal is optimized by using a fiber bundle having a diameter equal to that of the magnified image of the area over which the sample is irradiated. This arrangement maximizes the depth of field for Raman collection at a given resolution (e.g. about 1 cm depth of field for 40 $cm^{-1}$ resolution) and minimizes the requirement for precise sample alignment. The laser wavelength deviation and collection fiber diameter (which determines the effective reentrance slit-width) are chosen to provide a resolution that matches the intrinsic widths of the Raman signal spectral features. The exit ends 63 of the fibers in bundle 62 are positioned to lie in a single line stacked to match the dimensions of an entrance end 82 of a spectrograph 84 located in console 16, shown diagrammatically in FIG. 7. A spectrograph 84 suitable for use with the present invention is a 150 mm folded beam spectrometer, but a 0.275 m or 0.15 m spectrograph may also be used in accordance with the present invention. The single line defined by the exit ends 63 of fiber bundle 62 is parallel to the ruled lines on grating 83 within the spectrograph 84. The ruled grating 83 causes the Raman signal (and other accompanying light) to be dispersed into its spectral components onto the optical detector array 86. A suitable detector array for use in the present invention is a Princeton Instruments model RTE/CCD-256 spectrometric detector. The detector 86 is controlled by computer 60 in conjunction with trigger circuit 68 so that data collection is initiated as the laser source pulse begins to rise from the lower threshold intensity to the specified upper intensity. The initiation of data collection can be achieved by opening a shutter to the CCD array detector 86. The detector 86 collects the Raman spectrum and stores the resulting digital record as an image during a period of time specified by CCD controller 87. The image is subsequently read out to computer 90 for further processing in accordance with the present invention. The computer 90 usable in the present invention is an IBM 233 Mhz 128 megabyte computer handled through CCD controller 87. The typical command to recognition time is about 1 second.

Computer 90 employs a background subtraction routine that uses an entire baseline determination that is adaptive, in which peaks are actively searched for and the base is established between the peaks over the full spectrum. In addition, computer 90 processes the Raman signal image read from the array detector 86 with a second-derivative vector with high dimensional multi-variant projection. The vector is essentially n-dimensional where n is the number of pixels in the detector array 86. The computer 90 uses image processing routines to reduce the collected spectra to mathematical objects that resemble universal bar codes for comparison with mathematical objects scored in the library. The identification algorithm generates a numerical index between 1 and 0. Any value above the user-supplied threshold results in a positive identification which is displayed to the monitor screen. A value below threshold, or two values within a specified interval of each other produces a result of no identification as generally depicted in the flow chart in FIG. 8.

Figure 9A:
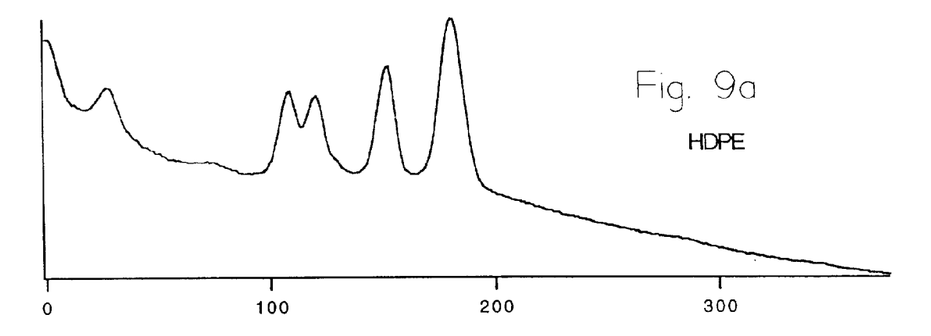
FIGS. 9a–9c are Raman spectra of selected materials.
Figure 9B:
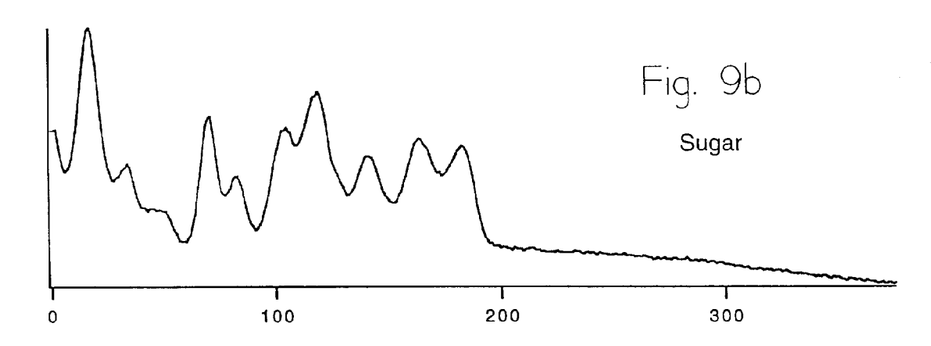
Figure 9C:
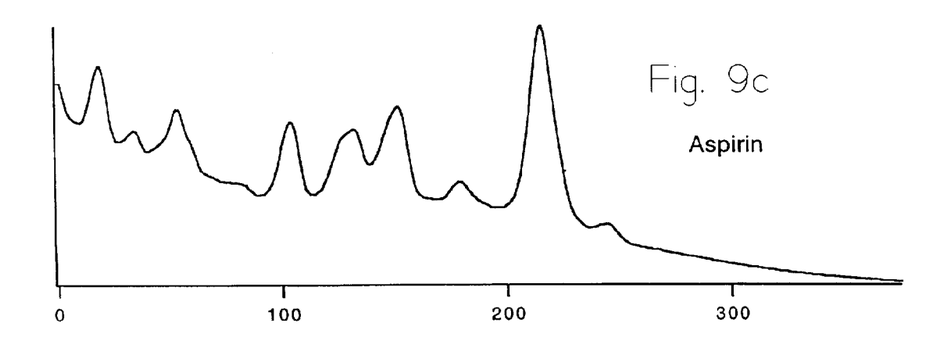
Figure 10A:
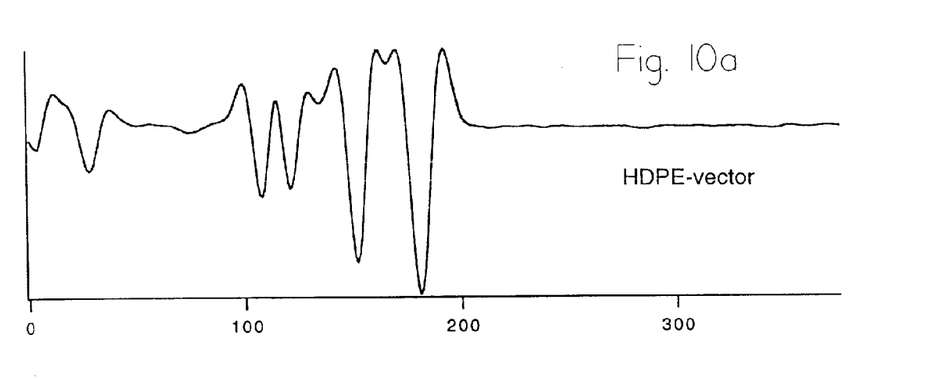
FIGS. 10a–10c are diagrams of corresponding second derivative vectors employed by the present invention.
Figure 10B:
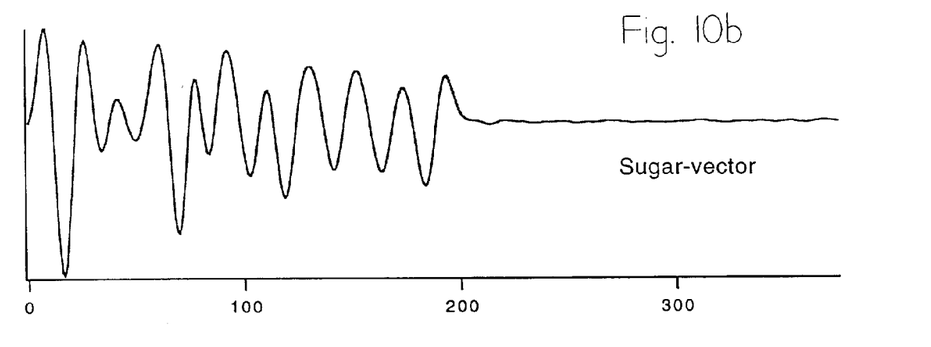
Figure 10C:
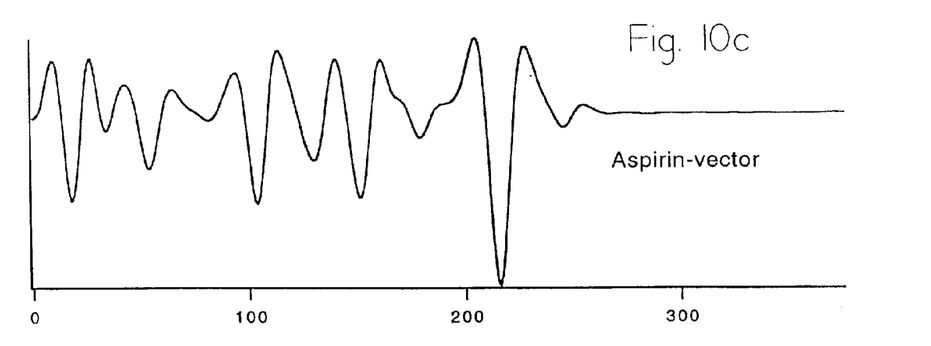

As a starting point, the computer 90 is loaded with a library of images taken from materials of known composition. The library can be user-extended to an arbitrary number of different materials. The basis for identification of a sample the Raman spectrum which, as illustrated in FIGS. 9a through 9c, are quite distinctive for different materials. The Raman spectrum appears as light that is shifted to longer wavelengths from the source laser. The observed wavelength shifts are produced by molecular vibrational fundamentals of various materials. These Raman spectral features typically appear as 5–50 peaks each of whose widths are less than or comparable to the spacing between peaks. As between samples of the same material, the spectral features are identical but the intensity of the features may vary depending upon the character of the light source causing the material to produce the Raman spectrum. To overcome this variation, the second-derivative vector is computed as shown in FIGS. 10a though 10c for the same materials as shown in FIGS. 9a through 9c. The second-derivative vector of the spectral information allows a number of mathematical operations to be performed on the information taken from the sample.

To load the library, an ambient light reading is taken by the probe and the image is detected by the detector 86. The image detected by the detector 86 is then processed by computer 90 to develop the second-derivative vector which is stored in the computer. Each of the materials of known composition is exposed to the probe 20 and the second-derivative vector for each known material is computed. The second derivative vector for the ambient light is then subtracted from the second-derivative vector of each of the materials of known composition and the difference stored with an identification of each known material in the library. The subtraction can be performed by redefining the library vectors so that they are made orthogonal to the ambient light vector. The subtraction can also be performed by a masking operation consisting essentially of identifying portions of the ambient vector where the value is above a selected criterion, and storing a zero value for such regions so that only areas outside those regions can be employed for comparison and identification. Other vector subtraction operations can be used without departing from the present invention.

Figure 8:
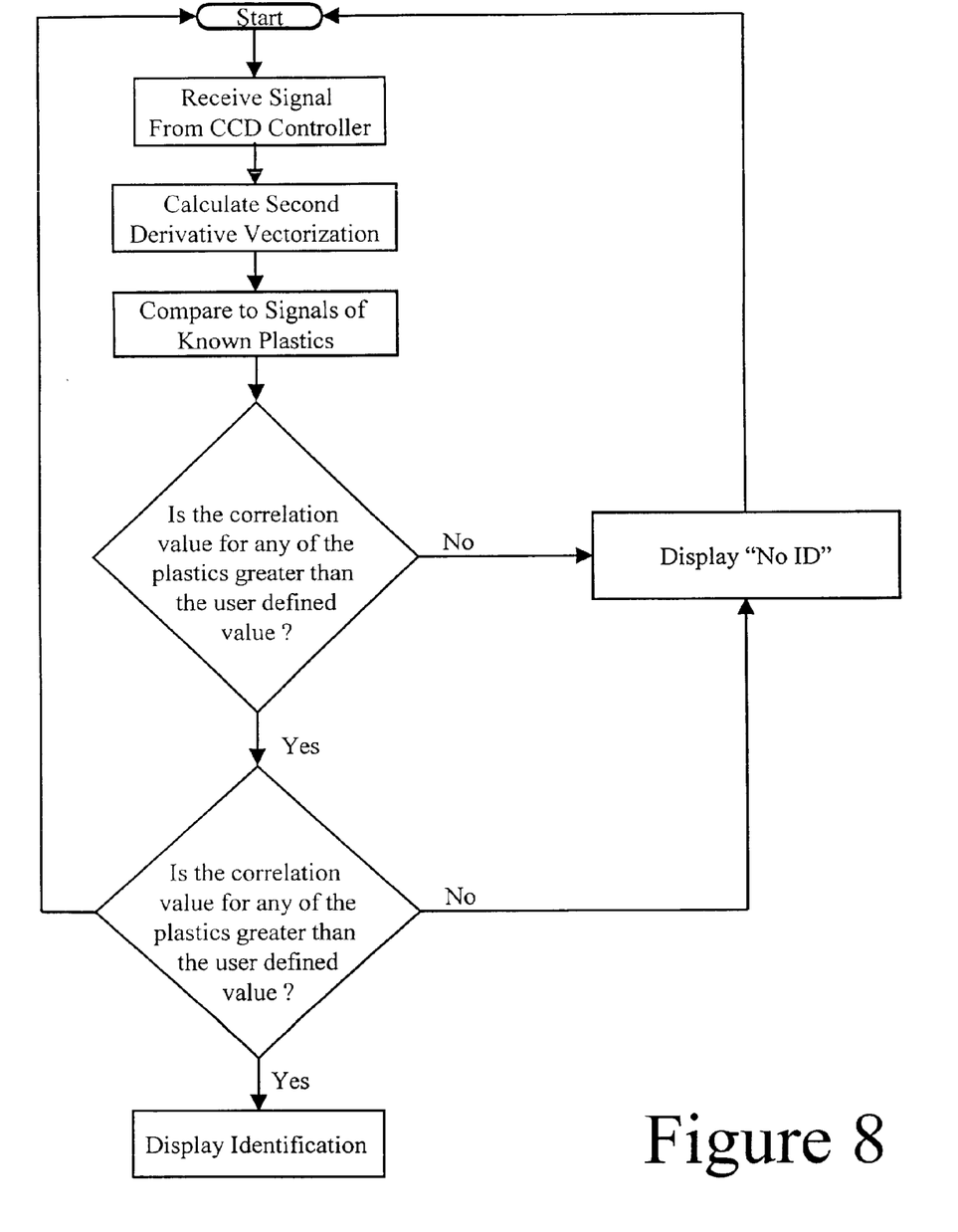
FIG. 8 is a flow diagram of the identification method of the present invention.

The identification of the composition of a material is achieved by performing the operation outlined in FIG. 8. The trigger 30 on handle 28 of the probe 12 is depressed as the probe is positioned less than 1 cm from a sample of an unknown composition. This initiates the acquisition of a Raman signal from the material and its detection by the array detector 86. The second-derivative vector is then computed and the ambient light vector is subtracted. The resulting sample vector is then compared to the library of vectors. While a number of mathematical operations can be employed for this comparison step, the preferred method is to compute the dot product of the sample vector with each library vector. The dot product yealds a scalar number that can be considered as a correlation value where 1 is perfect correlation of the two vectors and 0 is perfect anti-correlation. While one could merely look at the entire library for the highest correlation value, such a method might not always have the reliability one would want. In the preferred embodiment, an initial collection of identification candidates is assembled by merely collecting all library vectors having a correlation with the unknown sample above a user defined value. This collection is then surveyed to identify the top two library vectors and the difference in correlation values is computed for the top two vectors. If this difference in correlation value is greater than a user defined level, then the system has successfully discriminated between the two closest candidates, and the identification of the material is now known. If the difference in correlation values is very small then no unique material identification is possible without gathering additional data. Using the present invention plastics are now identified with typical correlations of about 0.95 or better against 0.20 or less for misses.

Although the chemical information content in a Raman spectrum is similar to that in a MIR spectrum, Raman scattering is superior to MIR in having a greater penetration depth (about 100 m to 1 cm for Raman as opposed to 1 m to 10 m for MIR). This larger penetration depth makes Raman sampling less sensitive to surface roughness and contamination than MIR. Furthermore, the fiber-bundle signal collection system makes the device 10 far less sensitive to precise placement of the plastic sample (positioning insensitivity within 1 cm for the device, as compared to less than 0.01 cm for the Bruker MIR instrument).

Raman spectral features are significantly sharper and better separated than NIR spectral features. Thus the chemical information content of a Raman spectrum is higher than a NIR spectrum. This higher information content not only allows identification to be performed with a lower error rate, but in addition makes it possible to qualitatively determine the chemical composition of copolymers and composites with a higher degree of accuracy than MIR.

EXAMPLE 1

Tests began with an examination of interior door panels. No problems occurred distinguishing ABS material from polypropylene (PP) in samples from beige to charcoal gray. Distinguishing PP from polyethylene (PE) fluid was absolutely routine, even in full room lights.

EXAMPLE 2

Plastic purgings composed of polycarbonate (PC) and ABS were identified. These were characterized only with great effort by a Bruker P/ID-22 FTIR system. The Bruker consistently labeled the sample PC+ABS. To examine this disagreement between the Bruker and the device in accordance with the present invention, a PC+ABS standard was added to the library in mid-test. This was a two key-stroke operation. Even with PC+ABS in the library, the purging consistently came back PC on the device. The Examine-Vector feature of the software was then used to compare the purging spectrum with library spectra of PC and PC+ABS at the second derivative level. The result was clear: The purging was unmistakably PC.

With PC and PMMA in our library, tail-lamp and head-lamp assemblies were sorted. Clear, amber and red lenses and light-colored backs were identified with 100% effectiveness.

Although the invention has been described in detail with reference to a preferred embodiment, variations and modifications exist within the scope and spirit of the invention as described and defined in the following claims.

What is claimed is:

1. Apparatus for identifying the composition of a sample, the apparatus comprising:
   a light source of known wavelength and deviation,
   radiation optics coupled to the light source so that light emitted from the light source is directed toward a sample causing the sample to produce a characteristic Raman spectrum,
   sampling optics situated to receive the characteristic Raman spectrum produced from the sample,
   a spectrograph coupled to the sampling optics for dispersing the characteristic Raman spectrum to form a spectrographic output, and
   an optical detector array coupled to the spectrograph to generate a digital map of the spectrographic output as a function of Raman shift wavelength, the width of the spectrum detected by each detector in the array is less than $\frac{1}{4}^{th}$ the excitation source wavelength deviation to permit smoothing of the spectrum detected by the discrete spectral elements to eliminate pixel noise without loss of Raman spectral information.

2. The apparatus of claim 1 wherein the spectrum detected by each detector in the array is greater than $\frac{1}{40}^{th}$ the light source wavelength deviation.

3. The apparatus of claim 1 further comprising a computer coupled to the detector including an input to receive the digital map, a user modifiable library of digital maps of specimens of known composition, a comparison means for comparing a received digital map with the contents of the library to select any match exceeding a specified confidence level, and an output display of the name of the selected match.

4. The apparatus of claim 1 further comprising a bandpass filter situated at an output of the light source to define further the deviation of the source.

5. The apparatus of claim 1 wherein the deviation of the source is less than 7 nm.

6. The apparatus of claim 1 wherein the radiation optics and sampling optics share a common holographic filter, the filter acting in the radiation optics to reflect the light emitted from the light source toward the sample, the filter acting in the sampling optics to block light at the wavelength of the light source from entry into the spectrograph.

7. The apparatus of claim 1 wherein the light source comprises a near-infrared laser operable in a pulse mode between a lower and an upper intensity, the lower intensity being at least as great as a threshold intensity below which laser activity is discontinuous, the upper intensity being any level at or below a maximum intensity established by the upper power limit of the laser.

8. The apparatus of claim 7 wherein the lower intensity is less than about 105% of the lasing threshold.

9. The apparatus of claim 7 wherein the pulse width defining the duration of the upper intensity is between about 0.01 and 10.0 seconds, and the number of pulses employed to test a given sample is selected in the range of from 1 to 10.

10. The apparatus of claim 1 wherein the radiation and sampling optics share a lens providing the apparatus with a prescribed depth of field so that the area irradiated by the radiation optics and the area from which the sampling optics receives the characteristic Raman spectrum is coincident.

11. Apparatus for identifying the composition of a sample, the apparatus comprising:
a probe including a housing having an optical window,
a monochromatic light source and radiation optics optically coupling the light source to the housing window so that light emitted from the light source is directed through the window toward a sample causing the sample to produce a characteristic Raman spectrum,
sampling optics coupled to the housing window to receive the characteristic Raman spectrum produced from the sample including at least one filter for removing unwanted spectral portions, the filter being included in the radiation optics to reflect the light emitted from the light source toward the sample,
a fiber bundle including a plurality of optical fibers, each of the fibers including an entrance end and an exit end, the entrance ends being situated in a compact array in a common plane within the probe housing so as maximally to collect the characteristic Raman spectrum, and the exit ends being arranged in a line,
a spectrograph having a slit opening coupled to the exit ends of the optical fibers in the fiber bundle for dispersing the characteristic Raman spectrum to form a spectrographic output of enhanced intensity while maintaining the required spectrographic resolution, and
an optical detector coupled to the spectrograph to generate a digital map of the spectrographic output as a function of Raman shift wavelength.

12. The apparatus of claim 1 wherein the radiation optics and sampling optics share a common holographic filter, the filter acting in the radiation optics to reflect the light emitted from the light source toward the sample, the filter acting in the sampling optics to block light at the wavelength of the light source from entry into the spectrograph.

13. The apparatus of claim 11 wherein the fiber bundle consists essentially of nineteen fibers arranged as a first fiber surrounded by six of the fibers which are in turn surrounded by twelve of the fibers.

14. The apparatus of claim 11 further comprising a computer coupled to the detector including an input to receive the digital map, a user modifiable library of digital maps of specimens of known composition, a comparison means for comparing a received digital map with the contents of the library to select any match exceeding a specified confidence level, and an output display of the name of the selected match.

15. The apparatus of claim 11 wherein the probe housing includes a handle to permit manipulation of the probe and further comprises a trigger coupled to the light source so that depression of the trigger at least temporarily increases the output of light from the source from a lower intensity to an upper intensity, the lower intensity being at least as great as a threshold intensity below which laser activity is discontinuous, the upper intensity being any level at or below a maximum intensity established by the upper power limit of the laser.

16. The apparatus of claim 11 wherein the spectrograph comprises a diffraction grating aligned with the line defined by the exit ends of the optical fibers.

17. The apparatus of claim 11 wherein the housing comprises an elongated rail having a lower and an upper surface and a tubular member including a longitudinal slot receiving the rail so that an axis of revolution of the tubular member is parallel to the rail upper surface and is aligned with said optical window.

18. The apparatus of claim 17 further comprising a plurality of supports fixed to the rail upper surface for supporting optical elements to intersect the axis of revolution, a back plate closing one end of the tubular member, and a nose cone closing another end of the tubular member, the nose cone containing the optical window.

19. The apparatus of claim 18 further comprising a band pass filter situated in the housing in spaced relation from the light source, and a baffling tube fixed within the housing contiguous to the band pass filter to form a segregated region within the housing for absorbing radiation reflected by the band pass filter.

20. The apparatus of claim 11 wherein the radiation optics and sampling optics share a lens providing a prescribed focal length for the incident light and a depth of field for the sampling optics so that small variations in position of the probe with respect to the sample surface have negligible effect on the Raman signal received by the fiber bundle.

21. A method for identifying the composition of a sample, the method comprising the steps of:
forming a plurality of pulses of light from a pulsed monochromatic light source so that the plurality of pulses contain between 0.05 and 0.5 joules of photon energy,
spacing the pulses from each other in time by a lapse time sufficient to allow thermal dissipation in the sample,
directing the plurality of pulses of light toward a sample so that the sample is illuminated by a peak power of less than 10.0 W/mm$^2$ so that a characteristic Raman spectrum is produced, and
capturing with a detector the characteristic Raman spectrum produced from the sample in such a manner as to permit comparison of the spectrum with spectra of specimens of known composition thereby identifying the composition of the sample.

22. The method of claim 21 wherein the capturing step comprises:
dispersing the characteristic Raman spectrum in a spectrograph to form a spectrographic output,
generating a sample digital map of intensity as a function of Raman shift wavelength using an optical detector coupled to the spectrograph to receive the spectrographic output, comparing the sample digital map with the contents of a user modifiable library of digital maps of specimens of known composition, selecting any match exceeding a specified confidence level, and displaying the name of the selected match.

23. The method of claim 21 further comprising the steps of: calculating a derivative vector of the Raman signal as a function of Raman shift wavelength, and computing a vector dot product of the derivative vector of the sample with each specimen vector stored in the library.

24. The method of claim 22 further comprising the steps of retaining the identification of all library stored vectors for which the vector dot product was greater than a specified value, and reviewing additional criteria of the sample vector and the retained library vectors to select the best fit.

25. The method of claim 21 wherein the directing step comprises the steps of:

operating a laser at a first intensity just above the threshold defining continuous operation, and triggering the laser to form a higher intensity pulse of less than ten second in duration, the duration of each pulse being short enough to avoid sample damage and detector saturation.

26. The method of claim 21 wherein the capturing step comprises the steps of:

focusing the characteristic Raman spectrum on a first end of a close-packed optical fiber bundle of at least seven fibers and arranging a second end of the fibers of the optical fiber bundle in a line at an input of a spectrograph.

27. A method for identifying the composition of a sample, the method comprising the steps of:

directing light from a monochromatic light source toward a sample so that the sample produces a characteristic Raman spectrum, capturing the characteristic Raman spectrum produced from the sample, capturing a signal representative of the ambient light in the vicinity of the sample over the wavelength range occupied by said characteristic Raman spectrum, dispersing the characteristic Raman spectrum in a spectrograph to form a sample spectrographic output, dispersing the ambient light signal in said spectrograph to form an ambient spectrographic output, generating a sample vector of the characteristic Raman spectrum as a function of Raman shift wavelength using an optical detector coupled to the spectrograph to receive the spectrographic output, generating an ambient vector of the background spectrum as a function of Raman shift wavelength using said optical detector coupled to the spectrograph to receive the spectrographic output, subtracting at least part of the ambient vector from the sample vector to form a normalized sample vector, comparing the normalized sample vector with the contents of a user modifiable library of vectors of specimens of known composition, selecting any match exceeding a specified confidence level, and displaying the name of the selected match.

28. The method of claim 27 wherein the subtracting step is performed by the steps of: identifying portions of the ambient vector where the value of the mapped variable is above a selected criterion, submasking the sample vector over said identifying portions to a zero value, and using only the remainder of the sample vector as the normalized sample vector.

29. The method of claim 27 wherein the subtracting step is performed by the steps of: redefining the library vectors so that they are made orthogonal to the ambient light vector, and comparing the redefined library of vectors with a sample vector that has been similarly orthogonalized.

30. A method for identifying the composition of a sample, the method comprising the steps of:

forming a pulse of light from a pulsed monochromatic light source so that the pulse contains between 0.05 and 0.5 joules of photon energy, directing the pulse of light toward a sample so that the sample is illuminated by a peak power of less than 10.0 W/mm$^2$ so that a characteristic Raman spectrum is produced, and capturing the characteristic Raman spectrum produced from the sample in such a manner as to permit comparison of the spectrum with spectra of specimens of known composition thereby identifying the composition of the sample, the capturing step to be initiated at the same time or before the forming step so that information concerning the characteristic Raman spectrum is obtained when it is first produced and before any significant heating of the sample occurs.

* * * * *